US006762308B2

(12) United States Patent
Petersen

(10) Patent No.: US 6,762,308 B2
(45) Date of Patent: *Jul. 13, 2004

(54) METHOD FOR THE PREPARATION OF CITALOPRAM

(75) Inventor: Hans Petersen, Vanløse (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 10/237,145

(22) Filed: Sep. 5, 2002

(65) Prior Publication Data

US 2003/0092919 A1 May 15, 2003

Related U.S. Application Data

(63) Continuation of application No. PCT/DK01/00168, filed on Mar. 13, 2001.

(30) Foreign Application Priority Data

Mar. 13, 2000 (DK) .......................... 2000 00401
Mar. 14, 2000 (DK) .......................... 2000 00415

(51) Int. Cl.⁷ ............................................ C07D 307/87
(52) U.S. Cl. ................................................. 549/467
(58) Field of Search .......................................... 549/467

(56) References Cited

U.S. PATENT DOCUMENTS

| | | | | |
|---|---|---|---|---|
| 3,467,675 A | 9/1969 | Petersen et al. | ........ | 260/346.2 |
| 4,136,193 A | 1/1979 | Bogeso et al. | ........ | 424/285 |
| 4,650,884 A | 3/1987 | Bogeso | ........ | 549/467 |
| 4,943,590 A | 7/1990 | Boegesoe et al. | ........ | 514/469 |
| 5,296,507 A | 3/1994 | Tanaka et al. | ........ | 514/465 |
| 6,020,501 A | 2/2000 | Massonne et al. | ........ | 549/307 |
| 6,028,204 A | 2/2000 | Massonne et al. | ........ | 549/307 |
| 6,229,026 B1 | 5/2001 | Petersen | ........ | 549/467 |
| 6,258,842 B1 | 7/2001 | Petersen et al. | ........ | 514/469 |
| 6,291,689 B1 | 9/2001 | Petersen et al. | ........ | 549/467 |
| 6,310,222 B1 | 10/2001 | Ikemoto et al. | ........ | 549/467 |
| 6,365,747 B1 | 4/2002 | Dall'Asta et al. | ........ | 548/146 |
| 6,392,060 B2 | 5/2002 | Petersen et al. | ........ | 549/307 |
| 6,403,813 B1 | 6/2002 | Petersen et al. | ........ | 549/305 |
| 6,407,267 B1 | 6/2002 | Rock et al. | ........ | 549/467 |
| 6,420,574 B2 | 7/2002 | Petersen et al. | ........ | 549/467 |
| 6,426,422 B1 | 7/2002 | Petersen et al. | ........ | 549/467 |
| 6,433,196 B1 | 8/2002 | Ikemoto et al. | ........ | 549/469 |
| 6,441,201 B1 | 8/2002 | Weber | ........ | 549/468 |
| 2002/0004604 A1 | 1/2002 | Petersen et al. | ........ | 549/462 |
| 2002/0026062 A1 | 2/2002 | Petersen et al. | ........ | 549/467 |
| 2002/0035277 A1 | 3/2002 | Rock et al. | ........ | 549/467 |
| 2002/0040153 A1 | 4/2002 | Petersen | ........ | 549/467 |
| 2002/0061925 A1 | 5/2002 | Petersen et al. | ........ | 514/469 |
| 2002/0077353 A1 | 6/2002 | Petersen et al. | ........ | 514/469 |
| 2002/0087012 A1 | 7/2002 | Castellin et al. | ........ | 549/467 |
| 2002/0120005 A1 | 8/2002 | Villa et al. | ........ | 514/466 |
| 2002/0128497 A1 | 9/2002 | Bolzonella et al. | ........ | 549/467 |

FOREIGN PATENT DOCUMENTS

| | | | | |
|---|---|---|---|---|
| EP | 1 095 926 | 5/2001 | .......... | C07C/33/46 |
| WO | 98/19511 | 5/1998 | | |
| WO | 98/19512 | 5/1998 | | |
| WO | 98/19513 | 5/1998 | | |
| WO | 99/30548 | 6/1999 | | |
| WO | 00/11926 | 3/2000 | | |
| WO | 00/12044 | 3/2000 | | |
| WO | 00/13648 | 3/2000 | | |
| WO | 00/23431 | 4/2000 | ........ | C07D/307/87 |
| WO | 00/39112 | 7/2000 | ........ | C07D/307/87 |
| WO | 00/44738 | 8/2000 | ........ | C07D/307/88 |
| WO | 01/45483 | 6/2001 | | |
| WO | 01/47877 | 7/2001 | | |
| WO | 01/47909 | 7/2001 | ........ | C07D/307/87 |
| WO | 01/49672 | 7/2001 | ........ | C07D/307/87 |
| WO | 01/51477 | 7/2001 | ........ | C07D/307/87 |
| WO | 01/51478 | 7/2001 | ........ | C07D/307/87 |
| WO | 01/66536 | 9/2001 | ........ | C07D/307/87 |
| WO | 01/68628 | 9/2001 | ........ | C07D/307/87 |
| WO | 01/68630 | 9/2001 | ........ | C07D/307/87 |
| WO | 01/68631 | 9/2001 | ........ | C07D/307/87 |
| WO | 01/68632 | 9/2001 | ........ | C07D/307/87 |
| WO | 02/04435 | 1/2002 | ........ | C07D/307/87 |

OTHER PUBLICATIONS

Bigler, Allan et al., "Quantitative Structure–activity Relationships in a Series of Selective 5–HT uptake inhibitors," *Eur. J. Med. Chem.* 3:289–295 (1997).

U.S. patent application Ser. No. 10/183,958, filed Jun. 25, 2002.

U.S. patent application Ser. No. 10/186,337, filed Jun. 27, 2002.

U.S. patent application Ser. No. 10/191,808, filed Jul. 8, 2002.

U.S. patent application Ser. No. 10/232,944, filed Aug. 29, 2002.

U.S. patent application Ser. No. 10/233,132, filed Aug. 30, 2002.

U.S. patent application Ser. No. 10/238,907, filed Sep. 6, 2002.

U.S. patent application Ser. No. 10/228,388, filed Aug. 23, 2002.

U.S. patent application Ser. No. 10/238,843, filed Sep. 9, 2002.

U.S. patent application Ser. No. 10/242,804, Sep. 10, 2002.

Levy, L.F., "4–Aminophthalide and Some Derivatives", *J. Chem. Soc.* pp. 867–870 (1931).

Tirouflet, Jean, "Phtalide Substitués en 5", *Bull. Soc. Sci. de Bretagne* 26:35–43 (1951).

Forney, LeRoy S.., "Reaction of Terephthalic Acid with Formaldehyde in Sulfur Trioxide Media," *J. Org. Chem.* 35:1695–1696 (1970).

Dordor, Isabelle M. et al., "Reaction of Oxazolines with Phosphorus Oxychloride," *Tetrahedron Letters* 24:1437–1440 (1983).

Barton, Sir Derek et al., *Comprehensive Organic Chemistry. The Synthesis and Reactions of Organic Compounds*, vol. 2, pp. 1024–1025.

*Primary Examiner*—Bernard Dentz
(74) *Attorney, Agent, or Firm*—Darby & Darby

(57) ABSTRACT

The present invention relates to a method for the preparation of citalopram by alkylation of a 1-(4-fluorophenyl)-1,3-dihydroisobenzofurane derivative.

23 Claims, No Drawings

METHOD FOR THE PREPARATION OF CITALOPRAM

This application is a continuation of International application no. PCT/DK01/00168, filed Mar. 13, 2001. The prior application is hereby incorporated by reference in its entirety.

The present invention relates to a method for the preparation of the well-known antidepressant drug citalopram, 1-[3-(dimethylamino)propyl]-1-(4-fluorophenyl)-1,3-dihydro-5-isobenzofurancarbonitrile.

BACKGROUND OF THE INVENTION

Citalopram is a well-known antidepressant drug that has now been on the market for some years and has the following structure:

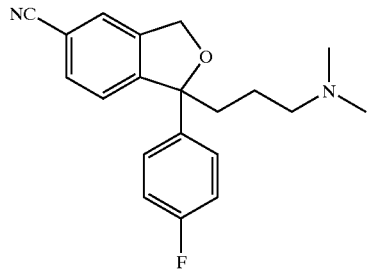

It is a selective, centrally acting serotonin (5-hydroxytryptamine; 5-HT) reuptake inhibitor, accordingly having antidepressant activities. The antidepressant activity of the compound has been reported in several publications, eg. J. Hyttel *Prog. Neuro-Psychopharmacol. & Biol. Psychiat.* 1982, 6, 277–295 and A. Gravem *Acta Psychiatr. Scand.* 1987, 75, 478–486. The compound has further been disclosed to show effects in the treatment of dementia and cerebrovascular disorders, EP-A-474580.

Citalopram was first disclosed in DE 2,657,013, corresponding to U.S. Pat. No. 4,136,193. This patent publication describes the preparation of citalopram by one method and outlines a further method, which may be used for preparing citalopram.

According to the process described, the corresponding 1-(4-fluorophenyl)-1,3-dihydro-5-isobenzofurancarbonitrile is reacted with 3-(N,N-dimethylamino)propyl-chloride in the presence of methylsulfinylmethide as condensing agent. The starting material was prepared from the corresponding 5-bromo derivative by reaction with cuprous cyanide.

International patent application No. WO 98/019511 discloses a process for the manufacture of citalopram wherein a (4-(cyano, alkyloxycarbonyl or alkylaminocarbonyl)-2-hydroxymethylphenyl-(4-fluorophenyl)methanol compound is subjected to ring closure. The resulting 5-(alkyloxycarbonyl or alkylaminocarbonyl)-1-(4-fluorophenyl)-1,3-dihydroisobenzofuran is converted to the corresponding 5-cyano derivative and the 5-cyano derivative is then alkylated with a (3-dimethylamino) propylhalogenide in order to obtain citalopram.

It has now, surprisingly, been found that citalopram may be manufactured by a novel favourable process where 5-cyano-1-(4-fluorophenyl)-1,3-dihydroisobenzofuran is alkylated with a compound which may be converted to a dimethylaminopropyl group.

The alkylation process according to the invention is particularly advantageous because the formation of by-products by polymerisation of the alkylating agent is avoided whereby a reduction in the amount of alkylating reagent to be used is made possible. The process of the invention provides high yields.

SUMMARY OF THE INVENTION

Thus, the present invention relates to a method for the preparation of citalopram comprising reaction of a compound of formula (I)

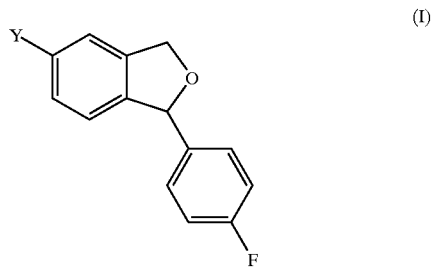

wherein Y is a group which may be converted to cyano, with a compound having the formula

wherein X is a suitable leaving group and R is —$CH_2$—O—Pg, —$CH_2$—$NPg_1Pg_2$, —$CH_2$—$NMePg_1$, —CO—N$(CH_3)_2$, —CH($A^1R^1$)($A^2R^2$), $COOR^3$, —$CH_2$—CO—$NH_2$, —CH=CH—$R^7$ or —$CONHR^8$, wherein Pg is a protection group for an alcohol group, $Pg_1$ and $Pg_2$ are protection groups for an amino group, $R^1$ and $R^2$ are independently selected from alkyl, alkenyl, alkynyl and optionally alkyl substituted aryl and aralkyl groups or $R^1$ and $R^2$ together form a chain of 2 to 4 carbon atoms, $R^3$ and $R^7$ are independently selected from alkyl, alkenyl, alkynyl and optionally alkyl substituted aryl and aralkyl, $R^8$ is hydrogen or methyl and $A^1$ and $A^2$ are selected from O and S;

to form a compound of the formula

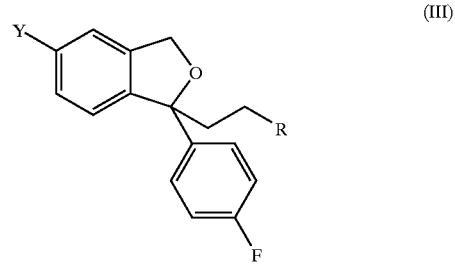

wherein R and Y are as defined above, followed by, in either order, conversion of the group R to a dimethylaminomethyl group and conversion of the group Y to a cyano group, followed by isolation of the citalopram base or a pharmaceutically acceptable acid addition salt thereof.

Thus, in one embodiment, the invention relates to a method for the preparation of citalopram wherein the compound of formula (I) is reacted with a compound of formula (II) wherein R is —$CH_2$—O—Pg to form a compound of formula

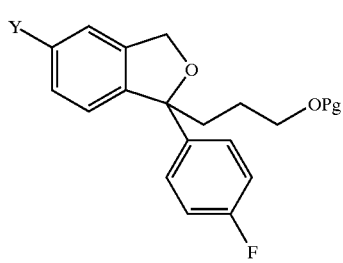

(IV)

wherein Y is a group which may be converted to cyano and Pg is a protection group for an alcohol group, optionally followed by conversion of the group Y to a cyano group; and thereafter removal of the protecting group to form a compound of formula

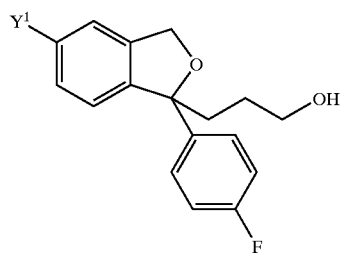

(V)

wherein $Y^1$ is cyano or a group which may be converted to cyano, and if $Y^1$ is not cyano, optionally followed by conversion of the group $Y^1$ to a cyano group; thereafter conversion of the alcohol group to a feasible leaving group, followed by, in either order, conversion of a group $Y^1$ which is not cyano to cyano, and replacement of the leaving group with a dimethylamino group by reaction with a) dimethylamine or a salt thereof,
b) methylamine followed by methylation or reductive amination, or
c) with an azide followed by reduction to form the corresponding amine and thereafter methylation or reductive amination.

In a second embodiment, the invention relates to a method for the preparation of citalopram wherein the compound of formula (I) is reacted with a compound of formula (II) wherein R is —CO—N(CH$_3$)$_2$ to form a compound of the formula

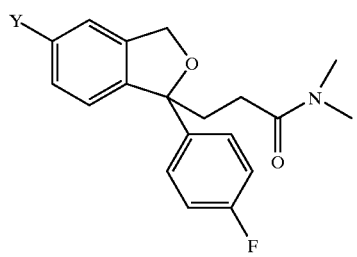

(VI)

wherein Y is as defined above, optionally followed by conversion of the group Y to a cyano group; and thereafter reduction of the resulting compound to form a compound of formula

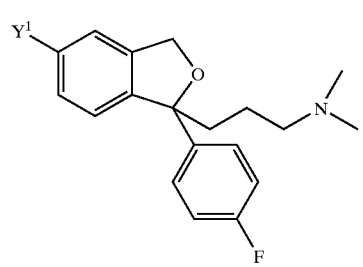

(VII)

wherein $Y^1$ is cyano or a compound which may be converted to cyano, and if $Y^1$ is not cyano conversion of the group $Y^1$ in the compound of formula (VII) to a cyano group.

In a third embodiment, the invention relates to a method for the preparation of citalopram wherein the compound of formula (I) is reacted with a compound of formula (II) wherein R is —CH$_2$—N(Pg$_1$)(Pg$_2$) to form a compound of formula

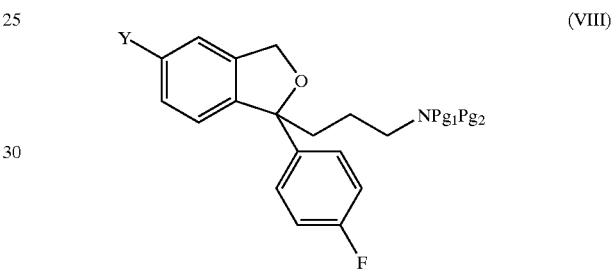

(VIII)

wherein Y is a group which may be converted to a cyano group and Pg$_1$ and Pg$_2$ are protection groups for an amino group, optionally followed by conversion of the group Y to a cyano group; and thereafter removal of the protecting groups to form a compound having the formula

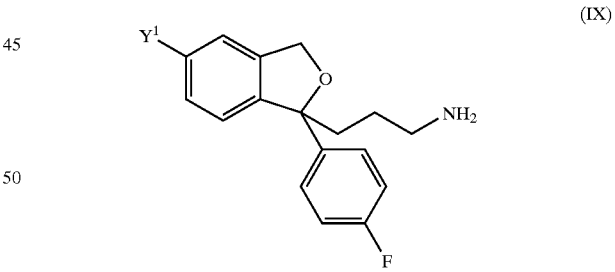

(IX)

wherein $Y^1$ is a cyano group or a group which may be converted to a cyano group, followed by, in either order, conversion of a group $Y^1$ which is not cyano to a cyano group and methylation or reductive amination of the free amino group to form citalopram.

In a fourth embodiment, the invention relates to a process for the preparation of citalopram wherein a compound of formula (I) is reacted with a compound of formula (II) wherein R is —CH(A$^1$R$^1$)(A$^2$R$^2$) to form a compound of the formula

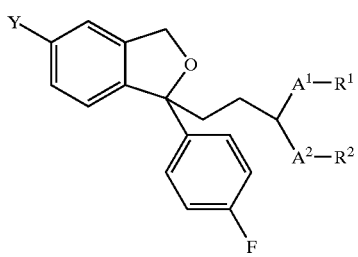

(X)

wherein Y is a group which may be converted to a cyano group, $R^1$ and $R^2$ are independently selected from alkyl, alkenyl, alkynyl and optionally alkyl substituted aryl and aralkyl groups or $R^1$ and $R^2$ together form a chain of 2 to 4 carbon atoms, and $A^1$ and $A^2$ are selected from O and S; optionally followed by conversion of the group Y to a cyano group; and thereafter deprotection of the compound of formula (X) to form a compound of formula

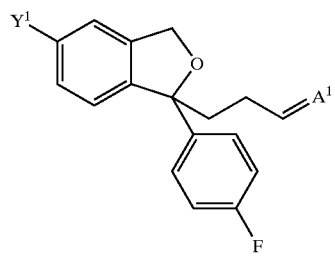

(XI)

wherein $Y^1$ is cyano or a group which may be converted to a cyano group and $A^1$ are as defined above, followed by, in either order, reductive amination with dimethylamine of the compound of formula (XI) and if $Y^1$ is not cyano, conversion of the group $Y^1$ to form a cyano group.

In a fifth embodiment, the invention relates to a method for the preparation of citalopram wherein a compound of formula (I) is reacted with a compound of formula (II) wherein R is —$COOR^3$ to form a compound of the formula

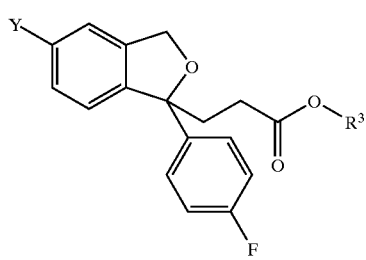

(XII)

wherein Y is a group which may be converted to cyano and $R^3$ is selected from alkyl, alkenyl, alkynyl and optionally alkyl substituted aryl and aralkyl, optionally followed by conversion of Y to a cyano group; and thereafter i) reduction to form an alcohol of formula (V)

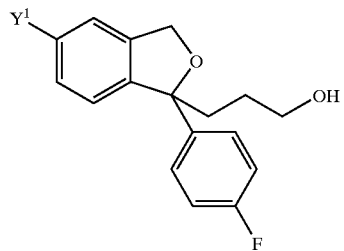

wherein $Y^1$ is cyano or a group which may be converted to cyano, and if $Y^1$ is not cyano, optionally followed by conversion of the group $Y^1$ to a cyano group; and thereafter conversion of the alcohol group to a feasible leaving group, followed by, in either order, conversion of a group $Y^1$ which is not cyano to cyano, and replacement of the leaving group with a dimethylamino group by reaction with a) dimethylamine or a salt thereof, b) methylamine followed by methylation or reductive amination, or c) with an azide followed by reduction to form the corresponding amine and thereafter methylation or reductive amination, or ii) reaction of a compound of formula (XII) with an amine of formula $NH(Me)_2$, $NH_2Me$ or $NH_3$ or a salt thereof to form an amide, followed by, in either order, reduction of the amide, and if $Y^1$ is not cyano, conversion of the group $Y^1$ to cyano, and if necessary methylation or reductive amination to form a dimethylamino group.

In a sixth embodiment, the invention relates to a method for the preparation of citalopram wherein a compound of formula (I) is reacted with a compound of formula (II) wherein R is —$CH_2$—CO—$NH_2$ to form a compound of the formula

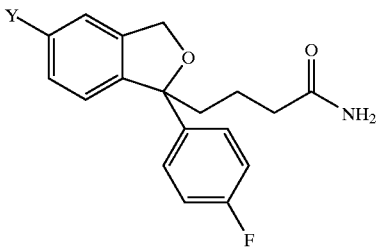

(XIII)

wherein Y is as defined above, optionally followed by conversion of Y to a cyano group; and thereafter treatment with a hypohalide to form a compound of formula

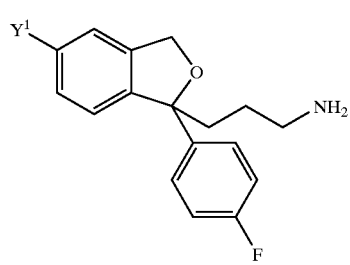

(IX)

wherein $Y^1$ is a cyano group or a group which may be converted to a cyano group, followed by, in either order, conversion of a group $Y^1$ which is not cyano to a cyano group and methylation or reductive amination of free amino group to form citalopram.

In a seventh embodiment, the invention relates to a method for the preparation of citalopram wherein a compound of formula (I) is reacted with a compound of formula (II) wherein R is —CH═CH—R⁷ to form a compound of the formula

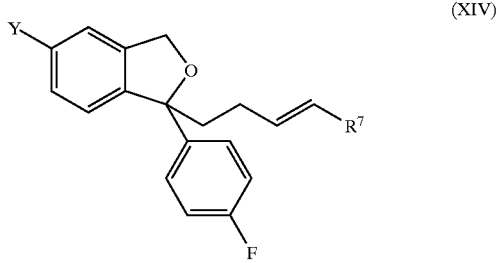

(XIV)

wherein Y is a group which may be converted to a cyano group and R⁷ is alkyl, alkenyl, alkynyl and optionally alkyl substituted aryl and aralkyl as defined above, optionally followed by conversion of the group Y to a cyano group; and thereafter oxidation to form a compound of formula

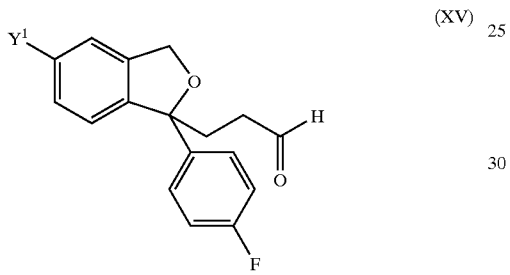

(XV)

wherein $Y^1$ is cyano or a group which may be converted to a cyano group, followed by, in either order, reductive amination with dimethylamine and if $Y^1$ is not cyano conversion of the group $Y^1$ to a cyano group to form citalopram.

In another embodiment, the invention relates to a method for the preparation of citalopram from a compound of formula

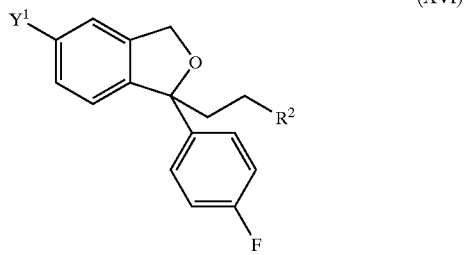

(XVI)

wherein $Y^1$ is a cyano group, or a group which can be converted to a cyano group and $R^2$ is —CH₂—W, wherein W is a leaving group, or $R^2$ is cyano or —CH₂N(CH₃)₂ comprising, in either order, conversion of the group $Y^1$ which is not cyano to a cyano group and conversion of the group $R^2$ which is not —CH₂N(CH₃)₂ to a dimethylaminomethyl group, followed by isolation of citalopram base or a pharmaceutically acceptable acid addition salt thereof.

According to this method, a group $R^2$ which is —CH₂—W, wherein W is a leaving group may be converted to a dimethylaminomethyl group by reaction with a) dimethylamine or a salt thereof, b) methylamine followed by methylation or reductive amination, or c) an azide followed by reduction to form the corresponding amine and thereafter methylation or reductive amination.

Further, according to this method a group $R^2$ which is cyano may be converted to a dimethylaminomethyl group by reduction followed by methylation or reductive amination of the free amino group formed. Reduction of the cyano group to an amino group may be carried out using using Rh, Raney Ni etc. as a catalyst.

The compound of formula (XVI) may be prepared by reaction of a compound of formula

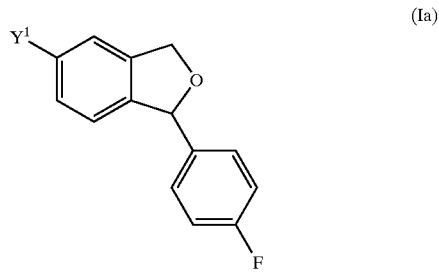

(Ia)

with a compound of formula

(IIa)

wherein X is a leaving group and $R^2$ is —CH₂—W, wherein W is a leaving group, or $R^2$ is cyano or —CH₂N(CH₃)₂; provided $R^2$ is not —CH₂N(CH₃)₂ when X is halogen and $Y^1$ is cyano, and if $Y^1$ is not cyano, optionally followed by conversion of the group $Y^1$ to a cyano group.

In a further embodiment, the invention relates to a method for the preparation of citalopram wherein a compound of formula (I) is reacted with a compound of formula (II) wherein R is —CH₂—NMe(Pg₁) to form a compound of formula

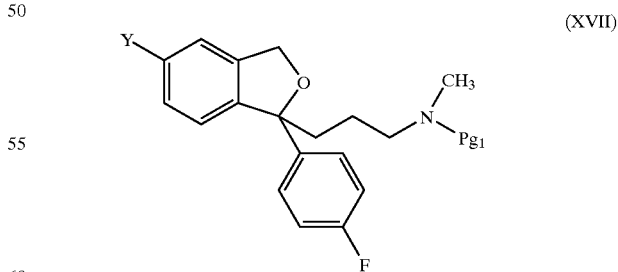

(XVII)

wherein Y is a group which may be converted to a cyano group and Pg₁ is a protection group for an amino group, optionally followed by conversion of the group Y to a cyano group; and thereafter removal of the protection group to form a compound of formula

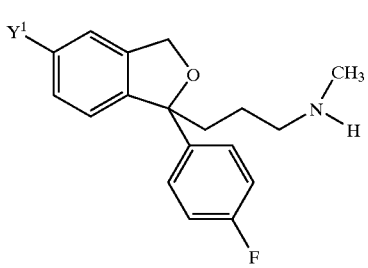

(XVIII)

wherein $Y^1$ is a cyano group or a group which may be converted to cyano, followed by, in either order, conversion of the group $Y^1$ which is not cyano to a cyano group and methylation or reductive amination of the amino group to form citalopram.

In still another embodiment, the invention relates to a process for the preparation of citalopram wherein a compound of formula (I) is reacted with a compound of formula (II) wherein R is —CO—NHR$^8$ to form a compound of formula

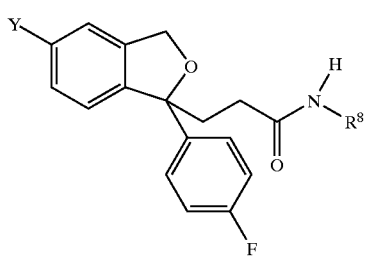

(XIX)

wherein Y is a group which may be converted to cyano and R$^8$ is hydrogen or methyl, optionally followed by conversion of the group Y to a cyano group; and thereafter reduction to form a compound of the formula

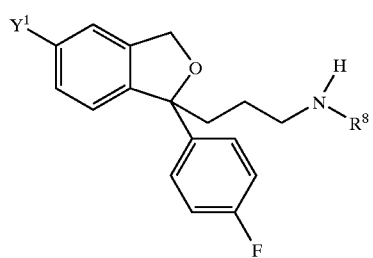

(XX)

wherein $Y^1$ is cyano or a group which may be converted to cyano and R$^8$ is hydrogen or methyl followed by, in either order, methylation or reductive amination to form the dimethylamino group and if $Y^1$ is not cyano, conversion of $Y^1$ to cyano.

In a further embodiment, the invention relates to a method for the preparation of citalopram comprising reaction of a compound of formula (Ia) with a compound of formula (II) wherein R is —C(A$^1$R$^4$)(A$^2$R$^5$)(A$^3$R$^6$) to form a compound of the formula

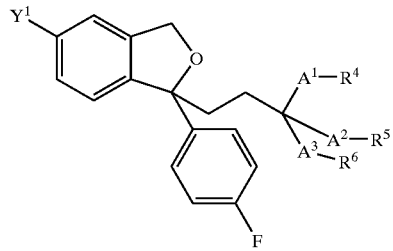

(XXI)

wherein $Y^1$ is a cyano group or a group which may be converted to cyano and wherein each of R$^4$, R$^5$ and R$^6$ are independently selected from alkyl, alkenyl, alkynyl and optionally alkyl substituted aryl and aralkyl and A$^1$, A$^2$ and A$^3$ is selected from O and S, and if $Y^1$ is not cyano optionally followed by conversion of $Y^1$ to a cyano group; and thereafter hydrolysis to form a compound of formula

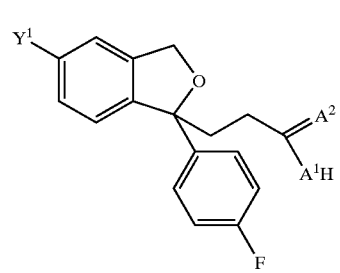

(XXII)

wherein $Y^1$ is cyano or a group which may be converted to cyano, and A$^1$ and A$^2$ is as defined above and if $Y^1$ is not cyano, optionally conversion of $Y^1$ to cyano; and followed by i) reduction of a compound of formula (XXII) or an ester thereof to form an alcohol of formula

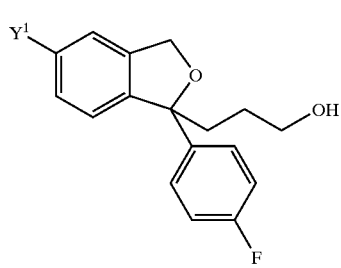

(V)

wherein $Y^1$ is cyano or a group which may be converted to cyano, and if $Y^1$ is not cyano, optionally followed by conversion of the group $Y^1$ to a cyano group; and thereafter conversion of the alcohol group to a feasible leaving group, followed by, in either order, conversion of a group $Y^1$ which is not cyano to cyano, and replacement of the leaving group with a dimethylamino group by reaction with a) dimethylamine or a salt thereof,
b) methylamine followed by methylation or reductive amination, or
c) with an azide followed by reduction to form the corresponding amine and thereafter methylation or reductive amination, or ii) conversion of a compound of formula (XXII) to an amide with an amine of formula NH(Me)$_2$, NH$_2$Me, NH₃ or a salt thereof, followed by, in either order, reduction of the amide, and if Y¹ is not cyano, conversion of the group Y¹ to cyano, and if necessary methylation or reductive amination to form a dimethylamino group.

The invention also relates to the intermediates having the formula (III), (XXI) and (XXII) and intermediates having the formula (V), (VII), (IX), (XVI), (XVIII) and (XI) wherein Y¹ is a group which may be converted to cyano.

In yet another aspect, the present invention relates to an antidepressant pharmaceutical composition comprising citalopram manufactured by the process of the invention.

The alkylation step where the compound of formula (I) and (Ia) are reacted with a compound of formula (II) and (IIa), respectively, is suitably carried out by treatment of the compound of formula (I) and (Ia) with a base such as for example LDA (lithiumdiisopropylamine), LiHMDS (hexamethyldisilasan lithium), NaH, NaHMDS (hexamethyldisilasan sodium) and metalalkoxides such as NaOMe, KOMe, LiOMe, NaOtertBu, KOtertBu and LiOtertBu in an aprotic organic solvent such as THF (tetrahydrofuran), DMF (dimethylformamide), NMP (N-methylpyrrolidon), ethers such as diethylether or dioxalane, toluene, benzene, or alkanes and mixtures thereof. The anion formed is then reacted with a compound of formula (II) or (IIa) whereby a group of formula —CH₂—CH₂—R and —CH₂—CH₂—R² is introduced into position 1 of the isobenzofuranyl ring system.

The reaction of the compound of formula (I) and (Ia) and with a compound of formula (II) and (IIa), respectively, is suitably carried out under non-aqueous conditions.

Suitable leaving groups X and W, may be a halogenide, or a sulphonate of formula —O—SO₂—R⁰ wherein R⁰ is alkyl, aralkyl, aryl or aryl substituted with alkyl. Conventionally, R⁰ is methyl or p-methylphenyl.

Groups Y which can be converted to a cyano group may be selected from halogen, —O—SO₂—(CF)ₙ—CF₃, wherein n is 0–8, —CHO, —COOR', —CONR'R", —NHR'" wherein R' and R" are hydrogen, alkyl, alkenyl or alkynyl, or optionally alkyl substituted aryl or aralkyl and R'" is hydrogen or alkylcarbonyl or Y is an an oxazoline or thiazoline group of the formula

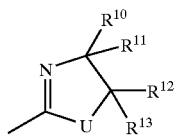

wherein

U is O or S;

$R^{12}$–$R^{13}$ are each independently selected from hydrogen and alkyl, or $R^{12}$ and $R^{13}$ together form a $C_{2-5}$ alkylene chain thereby forming a spiro ring; $R^{10}$ is selected from hydrogen and alkyl, $R^{11}$ is selected from hydrogen, alkyl, a carboxy group or a precursor group therefore, or $R^{10}$ and $R^{11}$ together form a $C_{2-5}$ alkylene chain thereby forming a spiro ring.

Y may be any other group, which can be converted to a cyano group.

The substituents $R^1$, $R^2$, $R^3$, $R^4$, $R^5$ and $R^6$ are preferably alkyl or aralkyl. Suitably, $R^1$ and $R^2$ and $R^4$, $R^5$ and $R^6$ are identical.

The alcohol protecting group, Pg, may be a trialkylsilyl group, a benzyl group or a tetrahydropyranyl group (THP).

According to the invention, the alcohol protecting group is removed to form the compound of formula (IV) using conventional methods for removal of the protection group in question.

Thus, where the protecting group is trialkylsilyl the protecting group may be removed by treatment with a base, an organic or mineral acid or a flouride such as KF, or trialkylaminoflouride.

Where Pg is benzyl, the protecting group may be removed by reduction using Pd/C or Pt/C as a catalyst.

Where Pg is a tetrahydropyranyl (THP) group, the protecting group may be removed by treatment with an organic or mineral acid, or resins carrying H⁺ groups such as Dowex H⁺ or Amberlyst.

The alcohol group in the compound of formula (V) is converted to a feasible leaving group such as halogen, or a sulphonate of formula —O—SO₂—R⁰ wherein R⁰ is as defined above, by reaction with reagents such as thionylchloride, mesylchloride, tosylchloride etc.

The resulting compound is then reacted with dimethylamine or a salt thereof, e.g. M⁺, N(CH₃)₂ wherein M⁺ is Li⁺ or Na⁺. The reaction is suitably carried out in an aprotic organic solvent such as THF (tetrahydrofuran), DMF (dimethylformamide), NMP (N-methyl pyrrolidon), ethers such as diethylether, or dioxalane, toluene, benzene, or alkanes and mixtures thereof. The compound of formula (V) carrying a suitable leaving group may also be converted to citalopram by reaction with dimethylammonium chloride in presence of a base. Alternatively, the compound of formula (V) carrying a suitable leaving group, such as a sulphonate of formula —O—SO₂—R⁰ wherein R⁰ is as defined above, may be reacted with an azide, such as sodium azide, followed by reduction using Pd/C as a catalyst to form a compound of formula (IX) and thereafter methylation or reductive amination to form Citalopram.

The compound of formula (V) carrying a suitable leaving group, may also be converted to citalopram by reaction with methylamine followed by methylation or reductive amination to form a dimethylamino group.

In a compound of formula (XVI) wherein $R^2$ is —CH₂—W wherein W is a suitable leaving group, W may be replaced by a dimethylamino group as described above.

The reduction of the amides of formula (VI) and (XIX) is conveniently carried out in toluene using Red-Al as a reducing agent.

Suitable groups $Pg_1$ and $Pg_2$ are aralkyl or —SO₂—R⁰ groups wherein R⁰ is as defined above, typically benzyl or tosyl, or $Pg_1$ and $Pg_2$ together with the N atom to which they are attached form an optionally substituted phthalimide group.

The protecting groups, $Pg_1$ and $Pg_2$, may be removed using conventional methods for removal of such protective groups. The phthalimide groups may thus be converted to an amino group by treatment with hydrazin or methylamine and ethanol.

Where the protecting group is an aralkyl group, such as benzyl, it may be removed by reduction, typically in presence of Pd/C or Pt/C as a catalyst.

Protecting groups of formula —SO₂—R⁰ may be removed by treatment with Red-Al.

The amino group in the compounds of formula (IX), (XVIII) and (XX) may be methylated with methylating agents such as MeI and Me₂SO₄, wherein Me is methyl. The methylation is carried out using conventional procedures for carrying out such reactions.

Alternatively, citalopram is formed by reductive amination. According to this procedure, the compound of formula (IX), (XVIII) or (XX) is reacted with compounds such as formaldehyde, paraformaldehyde or trioxan in the presence of a reducing agent such as NaBH₄ or NaBH₃CN. The reductive amination is carried out using conventional procedures for carrying out such reactions.

The compound of formula (Xa) or (Xb) may suitably be converted to the corresponding aldehyde by treatment with an organic or mineral acid or with resins carrying H+ groups such as Dowex H+ or Amberlyst.

The resulting aldehyde may be converted to citalopram by reductive amination, i.e. by reaction with dimethylamine in presence of a reducing agent such as NaBH$_4$ or NaBH$_3$CN.

The aldehydes of formula (XV) may be converted to a dimethylamino group by analogous methods.

The ester derivative of formula (XII) may be converted to citalopram via the corresponding alcohol of formula (V) by reduction of the ester using Red-Al as a reducing agent or via an amide by reaction of the ester with an amine, preferably NH$_2$(Me)$_2$ or a salt thereof. The reduction of the amide may suitably be carried out in toluene using Red-Al as reducing agent. Conversion of a free amino group or a monomethylamino group to a dimethylamino group may be carried out as described above.

Suitably, the agent useful for conversion of a compound of formula (XIII) to a compound of formula (IX) is NaOH/Br$_2$.

Oxidation of the compound of formula (XIV) may be carried out by treatment of the compound with ozone in a polar solvent such as alcohol, water, acetic acid or esters thereof. Alternatively, the compound of formula (XIV) may be treated with oxidation agents such as NaIO$_4$, OsO$_4$/NaIO$_4$ and KMnO$_4$.

Hydrolysis of a compound of formula (XXI) to form a compound of formula (XXII) may be carried out using mineral acids or organic acids.

Conversion of the compound of formula (XXII) to an alcohol of formula (V) or an amide may suitably be carried out via the corresponding acid chloride. The acid chloride may be prepared by treatment of the acid with POCl$_3$, PCl$_5$ or SOCl$_2$ neat or in a suitable solvent, such as toluene or toluene comprising a catalytic amount of N,N-dimethylformamide. The ester is obtained by treatment of the acid with an alcohol, in the presence of an acid, preferably a mineral acid or a Lewis acid, such as HCl, H$_2$SO$_4$, POCl$_3$, PCl$_5$ or SOCl$_2$. Alternatively, the ester may be obtained from the acid chloride by reaction with an alcohol.

The ester or the acid chloride is then converted to an amide of by amidation with ammonia or an alkylamine, preferably t-butyl amine.

The conversion to amide may also be obtained by reaction of the ester with ammonia or an alkylamine under pressure and heating.

The processes for the conversion of the corresponding alcohol or amide to the dimethylamino group of citalopram have already been described above.

When Y is halogen or CF$_3$—(CF$_2$)$_n$—SO$_2$—O—, wherein n is 0–8, the conversion to a cyano group may be carried out by reaction with a cyanide source, for example KCN, NaCN, CuCN, Zn(CN)$_2$ or (R$^{15}$)$_4$NCN, where (R$^{15}$)$_4$ indicates four groups, which may be the same or different, and are selected from hydrogen and straight chain or branched alkyl, in the presence of a palladium catalyst and a catalytic amount of Cu$^+$ or Zn$^{2+}$, or with Zn(CN)$_2$ in the presence of a palladium catalyst. The conversion of a compound wherein Y is halogen or CF$_3$—(CF$_2$)$_n$—SO$_2$—O—, wherein n is 0–8, by reaction with a cyanide source in the presence of a palladium catalyst, may be carried out as described in WO 0013648.

When Y is Cl or Br the conversion to a cyano group may also be carried out by reaction with a cyanide source, for example KCN, NaCN, CuCN, Zn(CN)$_2$ or (R$^{15}$)$_4$NCN, where (R$^{15}$)$_4$ indicates four groups, which may be the same or different, and are selected from hydrogen and straight chain or branched alkyl, in the presence of a nickel catalyst. The conversion of a compound wherein Y is halogen or CF$_3$—(CF$_2$)$_n$—SO$_2$—O—, wherein n is 0–8, by reaction with a cyanide source in the presence of a nickel catalyst may be carried out as described in WO 00/11926.

The reactions may be performed in any convenient solvent as described in Sakakibara et. al. *Bull. Chem. Soc. Jpn.* 1988, 61, 1985–1990. Preferred solvents are acetonitrile, ethylacetate, THF, DMF or NMP.

When Y is an oxazoline or a thiazoline of the formula (VI), the conversion to a cyano may be carried out as described in WO 00/23431.

When Y is CHO, the conversion to a cyano group may be carried out by conversion of the formyl group to an oxime or similar group by reaction with a reagent R$^{16}$—V—NH$_2$, wherein R$^{16}$ is hydrogen, alkyl, aryl or heteroaryl and V is O, N or S, followed by dehydration with a common dehydrating agent, for example thionylchloride, acetic anhydride/pyridine, pyridine/HCl or phosphor pentachloride. Preferred reagents, R$^{16}$—V—NH$_2$, are hydroxylamine and compounds wherein R$^{16}$ is alkyl or aryl and V is N or O.

When Y is —COOH, the conversion to a cyano group may be carried out via the corresponding acid chloride or ester and amide.

The acid chloride is conveniently obtained by treatment of the acid with POCl$_3$, PCl$_5$ or SOCl$_2$ neat or in a suitable solvent, such as toluene or toluene comprising a catalytic amount of N,N-dimethylformamide. The ester is obtained by treatment of the acid with an alcohol, in the presence of an acid, preferably a mineral acid or a Lewis acid, such as HCl, H$_2$SO$_4$, POCl$_3$, PCl$_5$ or SOCl$_2$. Alternatively, the ester may be obtained from the acid chloride by reaction with an alcohol. The ester or the acid chloride is then converted to an amide by amidation with ammonia or an alkylamine, preferably t-butyl amine.

The conversion to amide may also be obtained by reaction of the ester with ammonia or an alkylamine under pressure and heating.

The amide group is then converted to a cyano group by dehydration. The dehydrating agent may be any suitable dehydrating agent, and the optimal agent may easily be determined by a person skilled in the art. Examples of suitable dehydrating agents are SOCl$_2$, POCl$_3$ and PCl$_5$, preferably SOCl$_2$.

In a particularly preferred embodiment, the carboxylic acid is reacted with an alcohol, preferably ethanol, in the presence of POCl$_3$, in order to obtain the corresponding ester, which is then reacted with ammonia thereby giving the corresponding amide, which in turn is reacted with SOCl$_2$ in toluene comprising a catalytic amount of N,N-dimethylformamide.

Alternatively, a compound where Y is —COOH may be reacted with chlorosulfonyl isocyanate in order to form the nitrile, or treated with a dehydrating agent and a sulfonamide as described in WO 0044738.

When Y is —NHR'", where R'" is hydrogen, the conversion into cyano is preferably performed by diazotation and followed by reaction with CN$^-$. Most preferably NaNO$_2$ and CuCN and/or NaCN is used. When R'" is alkylcarbonyl, the compound is initially subjected to hydrolysis thereby obtaining the corresponding compound wherein R'" is H, which is then converted as described above. The hydrolysis may be performed either in acidic or basic environment.

Starting materials of formula (I) wherein X is halogen may be prepared as described in GB 1526331, compounds of formula (I) wherein X is —O—SO$_2$—(CF$_2$)$_n$—CF$_3$ may be prepared analogously to the compounds described in WO 99/00640, compounds of formula (I) wherein X is an oxazoline or a thiazoline group may be prepared analogous to the compounds described in WO 0023431, compounds wherein X is formaldehyde may be prepared analogously to the compounds described in WO 99/30548, compounds wherein X is —COOH, and esters and amides thereof may be prepared analogously to the compounds described in WO 98/19511 and compounds of formula I wherein is —NHR'" may be prepared analogously to the compounds described in WO 98/19512.

The reaction conditions, solvents, etc. used for the reactions described above are conventional conditions for such reactions and may easily be determined by a person skilled in the art.

The starting material of formula (Ia) wherein $Y^1$ is a cyano group may be prepared as described in U.S. Pat. No. 4,136,193 or as described in WO 98/019511.

The compounds of formula (II) and (IIa) are commercially available or may be prepared form commercially available starting materials using conventional techniques.

Citalopram is on the market as an antidepressant drug in the form of the racemate. However, in the near future the active S-enantiomer of citalopram is also going to be introduced to the market.

S-citalopram may be prepared by separation of the optically active isomers by chromatography.

Throughout the specification and claims, the term alkyl refers to a branched or unbranched alkyl group having from one to six carbon atoms inclusive, such as methyl, ethyl, 1-propyl, 2-propyl, 1-butyl, 2-butyl, 2-methyl-2-propyl, 2,2-dimethyl-1-ethyl and 2-methyl-1-propyl.

Similarly, alkenyl and alkynyl, respectively, designate such groups having from two to six carbon atoms, including one double bond and triple bond respectively, such as ethenyl, propenyl, butenyl, ethynyl, propynyl, and butynyl.

The term aryl refers to a mono- or bicyclic carbocyclic aromatic group, such as phenyl and naphthyl, in particular phenyl.

The term aralkyl refers to aryl-alkyl, wherein aryl and alkyl is as defined above.

The term optionally alkyl substituted aryl or aralkyl means aryl and aralkyl as above which are optionally substituted with one or more alkyl groups. Halogen means chloro, bromo or iodo.

Citalopram may be used as the free base, preferably in crystalline form, or as a pharmaceutically acceptable acid addition salt thereof. As acid addition salts, such salts formed with organic or inorganic acids may be used. Exemplary of such organic salts are those with maleic, fumaric, benzoic, ascorbic, succinic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The acid addition salts of the compounds may be prepared by methods known in the art. The base is reacted with either the calculated amount of acid in a water miscible solvent, such as acetone or ethanol, with subsequent isolation of the salt by concentration and cooling, or with an excess of the acid in a water immiscible solvent, such as ethylether, ethylacetate or dichloromethane, with the salt separating spontaneously.

The pharmaceutical compositions of the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvant or additive, colourings, aroma, preservatives etc. may be used provided that they are compatible with the active ingredients.

Solutions for injections may be prepared by solving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

The invention is further illustrated by the following examples.

EXAMPLE 1

A solution of 1-(4-fluorophenyl)-1,3-dihydroisobenzofuran-5-carbonitrile (4.8 g, 0.02 mol) in THF (50 ml) was added dropwise to a solution of LDA ( Butyl lithium 1.6 M (15 mL), disopropylamine 2.6 g) at −30° C. under an atmosphere of nitrogen. After stirring at −30° C. for 10 minutes, a solution of a compound of formula (II) or (IIa) (0.02 mol) in THF (25 mL) was added dropwise and allowed to warm to room temperature and stirred for a further 60 minutes. The reaction was then quenched with ice, extracted with toluene (3×50 mL), washed with water (50 mL) and concentrated under reduced pressure. The residue was purified by chromatography on silica gel using mixtures of n-heptane/EtOAc as the eluent.

What is claimed is:

1. A method for the preparation of citalopram comprising reacting a compound of formula (I)

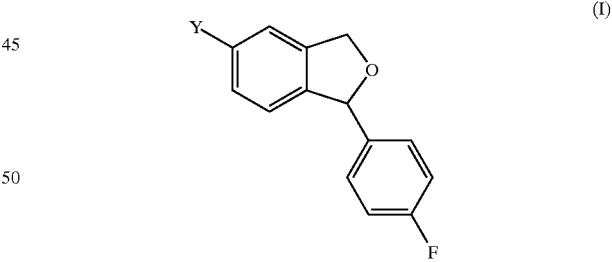

(I)

wherein Y is a group which may be converted to cyano, with a compound having the formula

(II)

wherein X is a suitable leaving group and R is —CH$_2$—O—Pg, —CH$_2$—NPg$_1$Pg$_2$, —CH$_2$—NMePg$_1$, —CO—N(CH$_3$)$_2$, —CH(A$^1$R$^1$)(A$^2$R$^2$), —COOR$^3$, —CH$_2$—CO—NH$_2$, —CH=CH—R$^7$ or —CONHR$^8$, wherein Pg is a protection group for an alcohol group, Pg$_1$ and Pg$_2$ are protection groups for an amino group, R$^1$ and R$^2$ are independently selected from alkyl, alkenyl, alkynyl and optionally alkyl substituted aryl or aralkyl groups or $R^1$ and $R^2$ together form a chain of 2 to 4 carbon atoms, each of $R^3$ and $R^7$ are independently selected from alkyl, alkenyl, alkynyl and optionally alkyl substituted aryl or aralkyl, $R^8$ is hydrogen or methyl and $A^1$ and $A^2$ are selected from O and S; to form a compound of formula

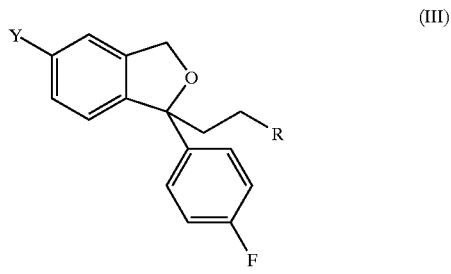

(III)

wherein R and Y are as defined above, followed by, in either order, converting R to a dimethylaminomethyl group and converting Y to a cyano group, followed by isolating citalopram base or a pharmaceutically acceptable acid addition salt thereof.

2. The method according to claim 1 wherein the compound of formula (I) is reacted with a compound of formula (II) wherein R is —$CH_2$—O—Pg to form a compound of formula

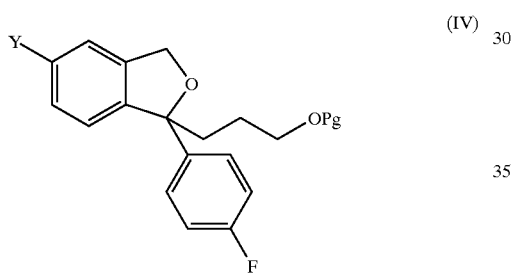

(IV)

wherein Y is a group which may be converted to cyano and Pg is a protection group for an alcohol group, optionally followed by converting Y to a cyano group; followed by removing the protecting group to form a compound of formula

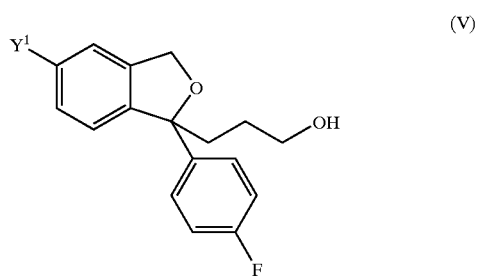

(V)

wherein $Y^1$ is cyano or a group which may be converted to cyano, and if $Y^1$ is not cyano, optionally followed by converting $Y^1$ to a cyano group; and thereafter converting the alcohol group to a feasible leaving group, followed by, in either order, converting $Y^1$ which is not cyano to cyano, and replacing the leaving group with a dimethylamino group by reacting with a) dimethylamine or a salt thereof,
b) methylamine followed by methylation or reductive amination, or
c) with an azide followed by reduction to form the corresponding amine and thereafter methylation or reductive amination.

3. The method according to claim 1 wherein the compound of formula (I) is reacted with a compound of formula (II) wherein R is —CO—$N(CH_3)_2$ to form a compound of the formula

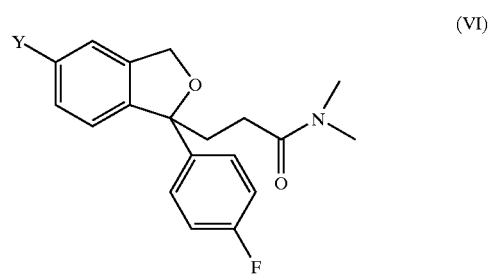

(VI)

wherein Y is as defined above, optionally followed by converting Y to a cyano group; and thereafter reducing the resulting compound to form a compound of formula

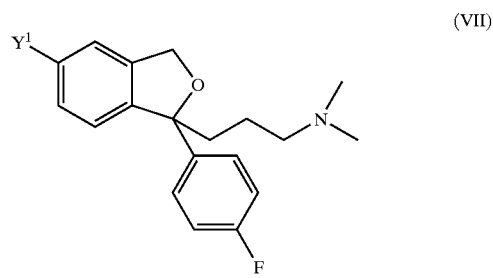

(VII)

wherein $Y^1$ is cyano or a compound which may be converted to cyano, and if $Y^1$ is not cyano converting $Y^1$ in the compound of formula (VII) to cyano.

4. The method according to claim 1 wherein the compound of formula (I) is reacted with a compound of formula (II) wherein R is —$CH_2$—$N(Pg_1)(Pg_2)$ to form a compound of formula

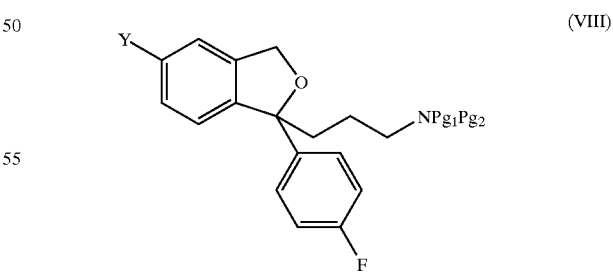

(VIII)

wherein Y is a group which may be converted to a cyano group and $Pg_1$ and $Pg_2$ are protection groups for an amino group, optionally followed by converting Y to a cyano group; and thereafter by removing the protecting groups to form a compound having the formula

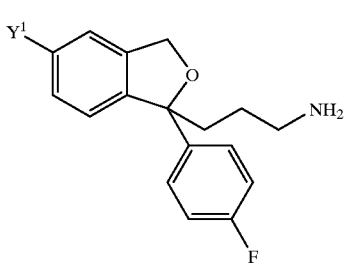

(IX)

wherein $Y^1$ is a cyano group or a group which may be converted to a cyano group, followed by, in either order, converting $Y^1$ which is not cyano to a cyano group and methylation or reductive amination of the free amino group to form citalopram.

5. The method according to claim 1 wherein a compound of formula (I) is reacted with a compound of formula (II) wherein R is —CH($A^1R^1$)($A^2R^2$) to form a compound of the formula

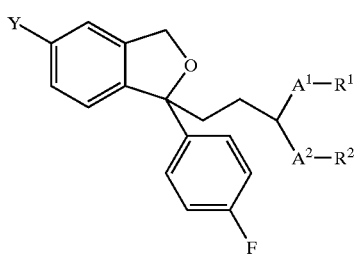

(X)

wherein Y is a group which may be converted to a cyano group, $R^1$ and $R^2$ are independently selected from alkyl, alkenyl, alkynyl and optionally alkyl substituted aryl and aralkyl groups or $R^1$ and $R^2$ together form a chain of 2 to 4 carbon atoms and $A^1$ and $A^2$ are selected from O and S; optionally followed by converting Y to a cyano group; and thereafter deprotecting the compound of formula (X) to form a compound of formula

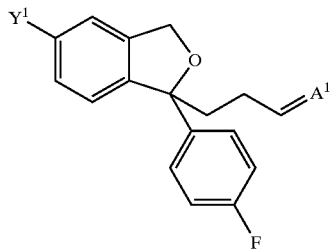

(XI)

wherein $Y^1$ is cyano or a group which may be converted to a cyano group and $A^1$ is as defined above, followed by, in either order, by reductive amination with dimethylamine of the compound of formula (XI) and if $Y^1$ is not cyano, converting $Y^1$ to form a cyano group.

6. The method according to claim 1 wherein a compound of formula (I) is reacted with a compound of formula (II) wherein R is —COOR³ where $R^3$ is as defined above to form a compound of the formula

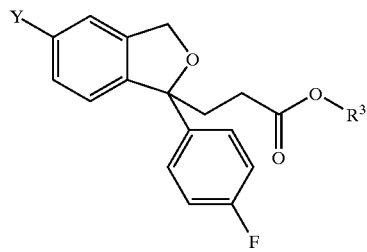

(XII)

wherein Y is a group which may be converted to cyano and $R^3$ is selected from alkyl, alkenyl, alkynyl and optionally alkyl substituted aryl and aralkyl, optionally followed by converting Y to a cyano group; and thereafter i) reduction to form an alcohol of formula

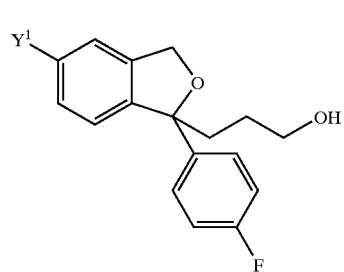

(V)

wherein $Y^1$ is cyano or a group which may be converted to cyano, and if $Y^1$ is not cyano, optionally followed by converting $Y^1$ to a cyano group; and thereafter converting the alcohol group to a feasible leaving group, followed by, in either order, converting $Y^1$ which is not cyano to cyano, and replacing the leaving group with a dimethylamino group by reaction with a) dimethylamine or a salt thereof,
b) methylamine followed by methylation or reductive amination, or
c) with an azide followed by reduction to form the corresponding amine and thereafter methylation or reductive amination, or ii) reacting the compound of formula (XII) with an amine of NH(Me)$_2$, NH$_2$Me, NH$_3$ or a salt thereof to form an amide, followed by, in either order, reducing the amide, and if $Y^1$ is not cyano, converting the group $Y^1$ to cyano, and if necessary methylation or reductive amination to form a dimethylamino group.

7. The method according to claim 1 wherein a compound of formula (I) is reacted with a compound of formula (II) wherein R is —CH$_2$—CO—NH$_2$ to form a compound of the formula

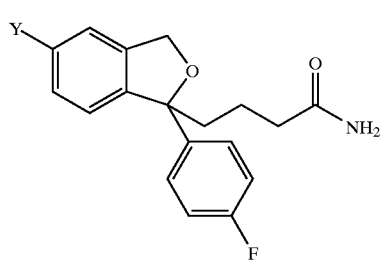

(XIII)

wherein Y is as defined above, optionally followed by converting Y to a cyano group; followed by treating the resulting compound with a hypohalide to form a compound of formula

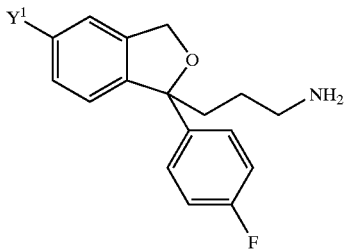

(IX)

wherein $Y^1$ is a cyano group or a group which may be converted to a cyano group, followed by, in either order, converting $Y^1$ which is not cyano to a cyano group and methylation or reductive amination of free amino group to form citalopram.

8. The method according to claim 1 wherein a compound of formula (I) is reacted with a compound of formula (II) wherein R is —CH=CH—$R^7$ to form a compound of the formula

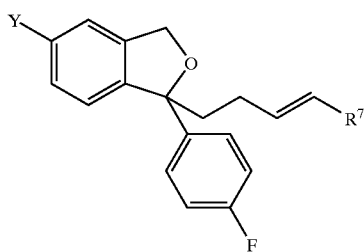

(XIV)

wherein Y is a group which may be converted to a cyano group and $R^7$ is alkyl, alkenyl, alkynyl and optionally alkyl substituted aryl and aralkyl as defined above, optionally followed by converting Y to a cyano group; and thereafter oxidizing the resulting compound to form a compound of formula

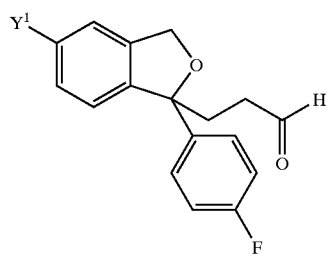

(XV)

wherein $Y^1$ is cyano or a group which may be converted to a cyano group, followed by, in either order, reductive amination with dimethylamine and if $Y^1$ is not cyano, converting $Y^1$ to a cyano group to form citalopram.

9. A method for the preparation of citalopram from a compound of formula

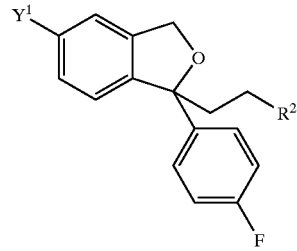

(XVI)

wherein $Y^1$ is a cyano group, or a group which can be converted to a cyano group and $R^2$ is cyano or —CH$_2$—W, wherein W is a leaving group, said method comprising, in either order, converting $Y^1$ which is not cyano to a cyano group and converting $R^2$ to a dimethylaminomethyl group, followed by isolating citalopram base or a pharmaceutically acceptable acid addition salt thereof.

10. The method according to claim 9 wherein $R^2$ is —CH$_2$—W, wherein W is a leaving group and the group W is replaced by a dimethylaminomethyl group by reacting with a) dimethylamine or a salt thereof,
b) methylamine followed by methylation or reductive amination, or
c) with an azide followed by reduction to form the corresponding amine and thereafter methylation or reductive amination.

11. The method according to claim 9 wherein group $R^2$ is cyano which is converted to a dimethylaminomethyl group by reduction followed by methylation or reductive amination of the free base of the amino group formed.

12. The method according to claim 9 wherein the compound of formula (XVI) is prepared by reacting a compound of formula

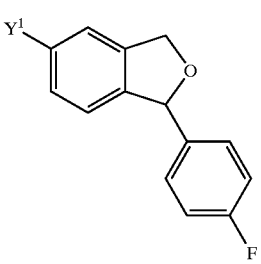

(Ia)

wherein $Y^1$ is a cyano group, or a group which can be converted to a cyano group, with a compound of formula

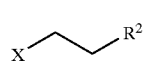

(IIa)

wherein X is a leaving group and $R^2$ is —CH$_2$—W, wherein W is a leaving group, or $R^2$ is cyano or —CH$_2$N(CH$_3$)$_2$; provided that $R^2$ is not —CH$_2$N(CH$_3$)$_2$ when X is halogen and $Y^1$ is cyano; and if $Y^1$ is not cyano, optionally followed by converting $Y^1$ to a cyano group.

13. The method according to claim 1 wherein the compound of formula (I) is reacted with a compound of formula (II) wherein R is —CH$_2$—NMe(Pg$_1$) to form a compound of formula

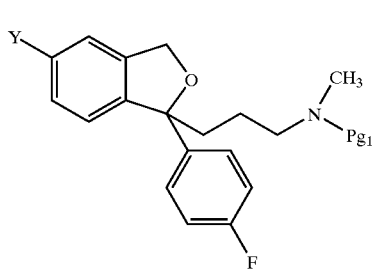

(XVII)

wherein Y is a group which may be converted to a cyano group and Pg₁ is a protection group for an amino group, optionally followed by converting Y to a cyano group; thereafter removing the protection group to form a compound of formula

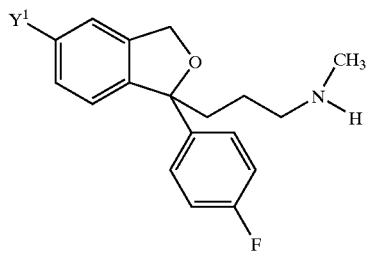

(XVIII)

wherein $Y^1$ is a cyano group or a group which may be converted to cyano, followed by, in either order, converting $Y^1$ which is not cyano to a cyano group and methylation or reductive amination of the amino group to form citalopram.

14. The method according to claim 1 wherein the compound of formula (I) is reacted with a compound of formula (II) wherein R is —CO—NHR⁸ to form a compound of formula

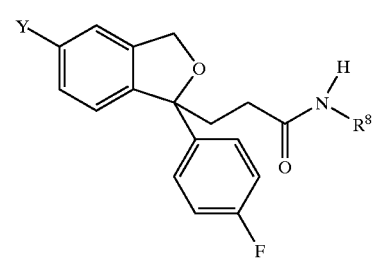

(XIX)

wherein Y is a group which may be converted to cyano and wherein R⁸ is hydrogen or methyl, optionally followed by converting Y to a cyano group; and thereafter reducing the resulting compound to form a compound of the formula

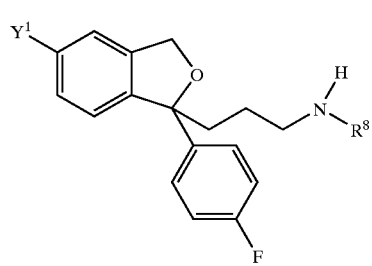

(XX)

wherein $Y^1$ is cyano or a group which may be converted to cyano and R⁸ is hydrogen or methyl, followed by, in either order, methylation or reductive amination to form a dimethylamino group, and if $Y^1$ is not cyano converting $Y^1$ to a cyano group.

15. A method for the preparation of citalopram, comprising reacting a compound of formula (Ia) with a compound of formula (II) wherein R is —C(A¹R⁴)(A²R⁵)(A³R⁶) to form a compound of the formula

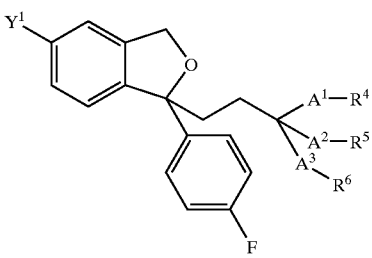

(XXI)

wherein $Y^1$ is a cyano group or a group which may be converted to cyano and wherein each of R⁴, R⁵ and R⁶ are independently selected from alkyl, alkenyl, alkynyl and optionally alkyl substituted aryl and aralkyl and A¹, A² and A³ are selected from O and S, if $Y^1$ is not cyano optionally followed by converting $Y^1$ to a cyano group; and thereafter hydrolysis to form a compound of formula

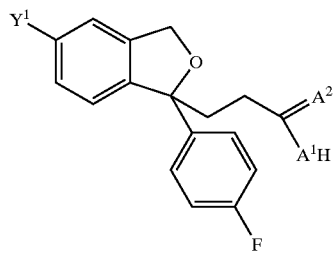

(XXII)

wherein $Y^1$ is cyano or a group which may be converted to cyano, and A¹ and A² are as defined above and if $Y^1$ is not cyano, optionally followed by converting $Y^1$ to cyano; and followed by i) reducing a compound of formula (XXII) or an ester thereof to form a compound of formula

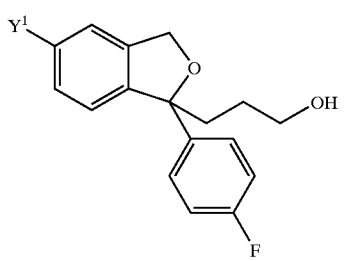

(V)

wherein Y¹ is cyano or a group which may be converted to cyano, and if Y¹ is not cyano, optionally followed by converting group Y¹ to a cyano group; and thereafter converting the alcohol group to a feasible leaving group, followed by, in either order, converting Y¹ which is not cyano to cyano, and replacing the leaving group with a dimethylamino group by reaction with a) dimethylamine or a salt thereof,
b) methylamine followed by methylation or reductive amination, or
c) with an azide followed by reduction to form the corresponding amine and thereafter methylation or reductive amination, or ii) converting the compound of formula (XXII) or an ester thereof to an amide followed by, in either order, reducing the amide, and if Y¹ is not cyano, Y¹ to cyano, and if necessary methylation or reductive amination to form a dimethylamino group.

16. A compound of the formula

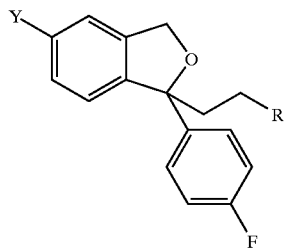

(III)

wherein Y is a group which may be converted to cyano and R is —CH$_2$—O—Pg, —CH$_2$—NPg$_1$Pg$_2$, —CH$_2$—NMePg$_1$, —CO—N(CH$_3$)$_2$, —CH(A$^1$R$^1$)(A$^2$R$^2$), —COOR$^3$, —CH$_2$—CO—NH$_2$, —CH=CH—R$^7$ or —CONHR$^8$, wherein Pg is a protection group for an alcohol group, Pg$_1$ and Pg$_2$ are protection groups for an amino group, R$^1$ and R$^2$ are independently selected from alkyl, alkenyl, alkynyl and optionally alkyl substituted aryl or aralkyl groups or R$^1$ and R$^2$ together form a chain of 2 to 4 carbon atoms, each of R$^3$ and R$^7$ are independently selected from alkyl, alkenyl, alkynyl and optionally alkyl substituted aryl or aralkyl, R$^8$ is hydrogen or methyl and A$^1$ and A$^2$ are selected from O and S; or an acid addition salt thereof.

17. A compound of formula

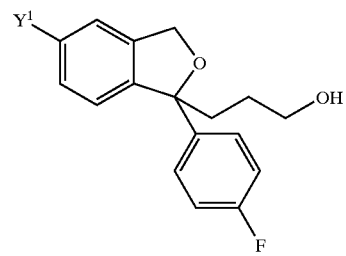

(V)

wherein Y¹ is a group which may be converted to cyano, or an acid addition salt thereof.

18. A compound of formula

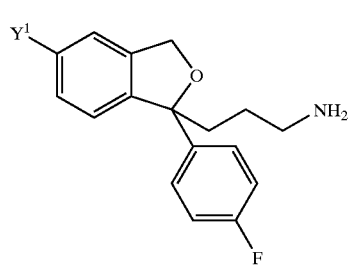

(IX)

wherein Y¹ is a compound which may be converted to cyano, or an acid addition salt thereof.

19. A compound of formula

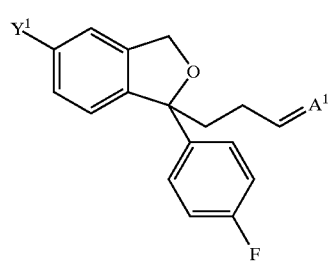

(XI)

wherein Y¹ is a group which may be converted to a cyano group and A$^1$ is O or S, or an acid addition salt thereof.

20. A compound of formula

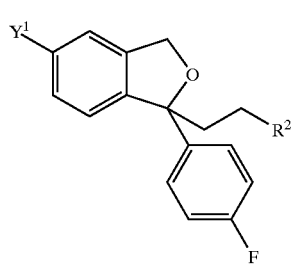

(XVI)

wherein Y¹ is a group which may be converted to a cyano group and R$^2$ is cyano or —CH$_2$—W, wherein W is a leaving group, or an acid addition salt thereof.

21. A compound of formula

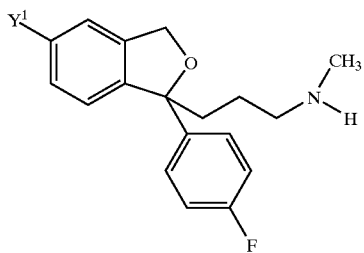

(XVIII)

wherein $Y^1$ is a group which may be converted to cyano, or an acid addition salt thereof.

22. A compound of formula

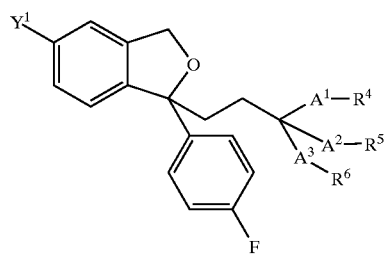

wherein $Y^1$ is a cyano group or a group which may be converted to cyano and wherein each of $R^4$, $R^5$ and $R^6$ are independently selected from alkyl, alkenyl, alkynyl and optionally alkyl substituted aryl and aralkyl and $A^1$, $A^2$ and $A^3$ are selected from O and S, or an acid addition salt thereof.

23. A compound of formula

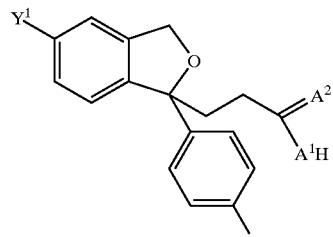

(XXII)

wherein $Y^1$ is cyano or a group which may be converted to cyano, and $A^1$ and $A^2$ is selected from O and S, or an acid addition salt thereof.

* * * * *